United States Patent [19]

Shihata

[11] 3,998,222
[45] Dec. 21, 1976

[54] SUBCUTANEOUS ARTERIO-VENOUS SHUNT WITH VALVE

[76] Inventor: Alfred A. Shihata, 2064 Baldwin, Jenison, Mich. 49464

[22] Filed: May 15, 1975

[21] Appl. No.: 577,933

Related U.S. Application Data

[63] Continuation-in-part of Ser. No. 460,789, April 15, 1974, abandoned.

[52] U.S. Cl. ............................ 128/214 R; 128/348; 128/274
[51] Int. Cl.² ........................................ A61M 5/00
[58] Field of Search ........ 128/214 R, 214 B, 214.2, 128/334 R, 334 C, 348, 350 R, 274

[56] References Cited
UNITED STATES PATENTS

| | | | |
|---|---|---|---|
| 3,198,195 | 8/1971 | Chardack | 128/419 P |
| 3,310,051 | 3/1967 | Schulte | 128/216 |
| 3,516,408 | 6/1970 | Montanti | 128/214 R X |
| 3,765,032 | 10/1973 | Palma | 128/214 R X |
| 3,826,257 | 7/1974 | Buselmeier | 128/214 R |
| 3,882,862 | 5/1975 | Berend | 128/214 R |

Primary Examiner—Dalton L. Truluck
Attorney, Agent, or Firm—McGarry & Waters

[57] ABSTRACT

A totally subcutaneous arterio-venous valved shunt, wherein no elements of the shunt are exposed supracutaneously, comprises a curved tubular shunt extending between an artery and a vein in a patient, with a pair of valves subcutaneously mounted in outlets in the shunt. The valves open and close fluid passages to the interior of the shunt upon axial movement of valve members. In use, a hollow needle is inserted through the patient's skin and mounted in an outlet opening in each valve member. The valve member is moved axially by the needle to open and close the valve and provide access to the blood flowing through the shunt. In a dialysis operation, blood is diverted to flow out of one (arterial) valve, through the dialyzer, and back through another (venous) valve of the subcutaneous shunt into the patient. Alternatively, one valve can be used for both outflow and inflow. On completion of dialysis, the valves are closed and the arterial and venous needles are withdrawn from the patient. When a single valve is used, a single needle suffices for both outflow and inflow.

22 Claims, 11 Drawing Figures

SUBCUTANEOUS ARTERIO-VENOUS SHUNT WITH VALVE

CROSS-REFERENCE TO RELATED APPLICATION

This application is a continuation-in-part of applicant's co-pending U.S. patent application entitled Subcutaneous Arterio-Venous Shunt With Valve, Ser. No. 460,789, Filed 4/15/74, now abandoned.

BACKGROUND OF THE INVENTION

1. Field of the Invention

This invention relates to a totally subcutaneous arterio-venous valved shunt particularly suitable for hemodialysis and a system for coupling a patient to a dialyzing apparatus.

2. Description of the Prior Art

An arterio-venous (AV) shunt is used for providing access to the bloodstream of a patient who requires substantial blood access treatment on a repeated or continuous basis. One of the principal uses of an arterio-venous shunt is in a kidney dialysis operation, wherein a patient's blood must be completely circulated through a dialysis machine as often as twice or three times a week for the entire life of a patient. The purpose of a shunt is to avoid the problems associated with repeated needle cannulation of a patient by providing at least one and preferably two "permanent" outlets from the bloodstream, so that blood can repeatedly be removed from the patient for treatment and then reintroduced into the bloodstream.

The shunt most commonly used for dialysis purposes comprises a pair of elongated tubular segments formed of silicone rubber (Silastic) which are surgically implanted in the arm or the groin of the patient. One tubular segment is connected to a vein and the other tubular segment is connected to an artery. Each tubular segment extends from the blood vessel through a convoluted loop underneath the skin and then protrudes through a continuously open hole in the skin to a fitting that dangles outside the body. The fittings on the outer ends of the tubular segments are constructed so that they may be connected together to provide a closed blood flow loop or separated and attached to a dialysis machine for circulating blood through the dialysis machine. The fittings are connected together to form a closed loop except when the patient is undergoing dialysis. When a patient is to be subjected to dialysis or other such blood treatment, the tubular segments are first clamped to stop the flow of blood, and then the fittings are separated and connected to the dialysis machine. The clamps are then released and blood is permitted to flow through the dialysis machine and back to the body.

Perhaps the most serious drawback with this type of shunt is that infection is a continual problem, both locally and generally. The risk of infection in this type of shunt is caused principally by the fact that the two supracutaneous outlets for connecting the shunt to a dialyzer require the existence of two continuously open holes in the skin. It is extremely difficult to prevent infection from eventually entering the body through these open holes, and the tissue surrounding these open holes is continuously irritated by the constant disturbance and moving of the tubular segments protruding through the holes. Antibiotics are employed to attempt to prevent or control infection, but when infection reaches serious proportions, it becomes necessary to surgically remove the entire shunt from the patient. Since there are only a limited number of acceptable shunt locations in the body, the loss of a shunt location is, in itself, a serious problem, aside from the problems and inconvenience involved in the act of removing one shunt and implanting another in a different location.

Another serious problem with prior art shunts of the nature described above, is that clotting of blood is a dominant risk. The clotting of blood is enhanced by several factors including infection, turbulance within the blood stream, temperature gradients in the blood stream, the stopping of blood flow, and blood flow resistance caused by rough interior tubular surfaces due to the presence of joints or curves in the shunt. When any of these conditions is present, the incidence of blood clotting in any given sampling of people is markedly increased. When a blood clot occurs in either of the tubular segments in the shunt of the prior art, it is frequently difficult or impossible to clear the blockage because of the fact that the tubular shunt follows a convoluted path under the skin, and this path has sharp turns which prevent a catheter from being fitted through the shunt. Thus, when such a shunt clogs, it is frequently necessary to surgically remove the entire shunt and implant a new shunt. This, of course, is undesirable, and the additional surgery and blood vessel work required in the patient increases the likelihood of infection or other harmful side effects.

With the foregoing prior art shunt, the risk of blood clotting is especially significant, because of the multiple curved construction of the shunt necessitated by the subcutaneous and supracutaneous elements and the joints employed in the shunt. The multiple sharp curves and the joints create excessive turbulence, and the supracutaneous portion of the shunt creates fluctuating temperature gradients as the blood flows inside and outside the body through the shunt.

Clotting may also occur with this type of shunt due to misalignment of the subcutaneous tips of the shunt with the blood vessels in which they are mounted. This is a significant problem with this type of shunt, because the anchorage of the shunt in the body is sustained primarily by the punctures through the skin which hold the shunt in position. Movement of clothing or other disturbance of the portion of the shunt that extends outside the body causes a continual disturbance to the shunt itself, and this disturbance is translated to the connections between the tips of the shunt and the blood vessels to which they are attached. Movement of the tips is also encouraged during the beginning and ending phases of the dialysis function, when manipulation of the external portions of the shunt is necessary.

Another reason why the foregoing prior art shunt enhances blood clotting is that the blood stream is completely stopped at the beginning and ending phases of dialysis, when it is necessary to clamp the tubular segments in order to connect and disconnect the fittings from the dialysis machine. This stoppage of blood flow greatly increases the prospects of blood clotting.

The problem with blood clotting is especially significant in home kidney dialysis operations, where a kidney dialysis patient performs the dialysis by himself at home. When a blood clot occurs in a patient's shunt, he has no recourse but to abandon the home treatment procedure and seek immediate corrective measures from his doctor.

Another disadvantage with a shunt of this nature is that the exposed outer connections make it possible for the shunt to become completely dislodged accidentally, and patients are required to limit movement for fear of causing an accidental dislodging or misalignment of the shunt. Further, continuous care is involved in a never ending attempt to keep the shunt clean and, as far as possible, free from infection. Still another drawback with a shunt of this nature is that the mere existence of the tubular loop dangling outside the body through open holes in the skin is cosmetically, as well as hygenically, undesirable.

Another type of shunt that has been developed comprises a U-shaped loop, one end of which is connected to a vein and the other end of which is connected to an artery. The loop itself may be mounted in the body subcutaneously, but outlet conduits extending from the sides of the loop protrude through open holes in the skin to outlet terminals on the outside of the body. Removable plugs fit in the outlet tubes and block the flow through these tubes during normal conditions. To subject a person to dialysis, the plugs are removed and the outlet terminals are connected to inlet fittings for a dialysis machine.

This type of shunt avoids certain of the problems with the other prior art shunt discussed above, namely, the shunt is substantially shorter and does not have the multiple curves of the prior shunt. However, several of the deficiencies of the other shunt are present in this shunt as well. One of the principal deficiencies is that this shunt still has outlets on the outside of the skin, and continuously open holes are still required in the skin to permit the shunts to extend through the skin. Thus, the most serious problem, infection, is still present. The likelihood of blood clotting in the outlet conduits in this type of shunt is substantial because the outlet conduits have to be clamped closed (causing blood stagnation at the beginning and end of dialysis). Further, any shunt having external outlets is subject to the problems of misaligning with the blood vessels in which it is mounted.

One of the principal objects of the present invention is to provide an arterio-venous shunt which is disposed completely below the surface of the skin of the patient so as to eliminate the problems of infection, clotting, and accidental dislodging of the shunt.

Another object of the present invention is to provide an arterio-venous shunt in a small and compact form, which is easy to install in a single piece in the limb of the patient.

Another object of the present invention is to provide an arterio-venous shunt which is positively self-stabilizing beneath the skin.

Still another object of the present invention is to provide an arterio-venous shunt that minimizes the incidence of blood clotting by (a) reducing blood flow turbulence; (b) reducing stagnation pockets in the shunt; (c) reducing blood flow resistance by reducing the total length of the shunt; and (d) eliminating temperature gradients in the blood flow.

It is the further object of the present invention to provide an arterio-venous shunt that can easily be declotted and cleaned by a conventional Fogarty catheter, in the event that clotting should ever occur in the shunt.

SUMMARY OF THE INVENTION

In accordance with the present invention, an improved arterio-venous valved shunt is implanted completely subcutaneously in a patient and provides for blood access to the patient by means of a hollow needle inserted through the skin of the patient. The valved shunt comprises a curved tubular member having one end or tip connected to an artery and the other end connected to a vein, with at least one subcutaneous outlet being formed in the side of the tubular member so as to provide fluid communication between the interior and the exterior of the shunt. A valve is mounted subcutaneously in the outlet, with the valve having an open position, wherein the outlet is open, and a closed position, wherein the outlet is blocked. The valve further comprises an outlet opening that is adapted to engage and receive the inner end of a hollow needle that is inserted through the skin so as to provide a closed conduit leading from the interior of the shunt to the outer end of the hollow needle when the valve is opened. The valve is opened and closed by the needle while it is in place in the valve, without providing an additional opening in the skin.

The valve of the present invention includes a hollow tubular housing mounted in the outlet of the shunt so as to define an opening between the interior and the exterior of the shunt. A movable valve member is mounted in the housing for longitudinal movement in the housing from an open position, wherein there is fluid communication between the interior and the exterior of the shunt, to a closed position, wherein the opening through the housing is blocked.

The valve member itself comprises a cylindrical member having an internal opening therethrough that extends from an outlet opening in the outer end thereof to an inner opening in the side of the valve member adjacent the inner end. In an aspect of the present invention, the valve member is threaded into the housing so that the rotation of the valve member causes the valve member to move longitudinally along the valve housing. To open the valve, the valve member is rotated in one direction, so that the valve member protrudes from the inner end of the housing into the interior of the shunt. This exposes the opening in the side of the valve member to the interior of the shunt and provides fluid communication between the interior and exterior of the shunt through the opening in the valve. To close the valve, the valve is rotated in the other direction. This retracts the valve member into the housing, blocking the opening in the side of the valve member.

To open and close the valve when the valved shunt is subcutaneously mounted in a patient, the outlet opening in the valve member is provided with a non-circular outer configuration, and a non-circular portion of similar outer configuration is formed adjacent the inner end of the hollow needle. Thus, when the needle is inserted into the outlet opening in the valve, the needle securely engages the valve member, so that the rotation of the needle causes the rotation and consequent opening and closing of the valve member. Thus, the valve of the present invention may be opened and closed with the needle in place in the outlet opening of the valve member without making any additional incisions or openings in the skin of the patient.

For ease in opening and closing the valve, the valve member and housing are interconnected by means of a double thread, and the full length of movement along this thread is adjusted so that the valve member becomes fully extended into the shunt upon the rotation of the valve member through an angle of 180°. When fully extended the opening in the side of the valve member is fully exposed, yet there is still sufficient room in the shunt to permit a smooth continuation of blood flow around the valve, thus avoiding stoppage or stagnation of blood flow in the shunt.

In a second embodiment of the valve mechanism of the present invention, the valve member is moved axially between its open and closed positions by sliding non-rotatably in the housing. To accomplish this, at least a portion of the exterior of the valve member has a non-circular configuration and this portion fits slidably in a housing having a like inner configuration. Collars are formed on the valve member to limit inward and outward movement of the valve member.

In this embodiment of the valve mechanism, the needle is mounted in the outlet of the valve member by means of a threaded connection, with the end of the needle being threaded into a threaded opening in the outlet.

The shunt is formed of silicone rubber tubing (Silastic), and the outlet means provided in the shunt is a short section of outlet tubing that extends outwardly at right angles from the shunt. When the sliding valve member is employed, the housing extends through only a portion of the outlet tubing, and the collars on the valve member on each side of the housing engages the tubing. This results in a frictional fit which holds the valve member in its desired axial position until the position is changed manually by movement of the hollow needle in engagement with the outlet opening.

When the valved outlet is being used for withdrawing blood from the individual, the valve is positioned in the outlet so that the opening in the side of the valve member is positioned in the outlet so that the opening in the side of the valve member faces directly upstream in the bloodstream when the valve is fully opened. This assures maximum efficiency in removing blood from the patient. Similarly, when the valved outlet is used for introducing blood or medication into the patient, the valve is positioned in the outlet so that it faces downstream in the bloodstream when it is fully opened.

A single valved outlet in the shunt would be sufficient for certain blood treatment and dialysis purposes wherein the purpose is to withdraw a portion of the blood or to introduce additional blood or medication into the bloodstream. However, for kidney dialysis purposes, a pair of valved outlets are preferable, with the outlets being spaced apart longitudinally along the shunt. The upstream valve is called the arterial outlet and the downstream valve is called the venous outlet.

One of the principal advantages of the present invention is that the problems of infection, blood clotting, and accidental dislodgement or misalignment are minimized by mounting the entire shunt subcutaneously in the individual. Further, the shunt is short and compact and is easy to surgically implant in the patient. Also, the shunt of the present invention obviates the problems of blood stagnation, temperature gradients, and turbulence, which further reduces the likelihood of blood clotting. Another advantage of the present invention is that in the event that blood clotting should ever occur, it is a simple procedure to eliminate the blockage by the use of a conventional Fogarty catheter, which may be inserted into the bloodstream through the hollow needle inserted in the outlet opening of the valve member.

The shunt of the present invention is also desirable for home dialysis purposes because it can be operated by a single individual at home, even if the individual suffers from a handicap such as poor eye sight.

These and other advantages and features of the present invention will hereinafter appear and for purposes of illustration but not of limitation, a preferred embodiment of the present invention is described in detail below.

DETAILED DESCRIPTION OF PREFERRED EMBODIMENTS

Figure 1:
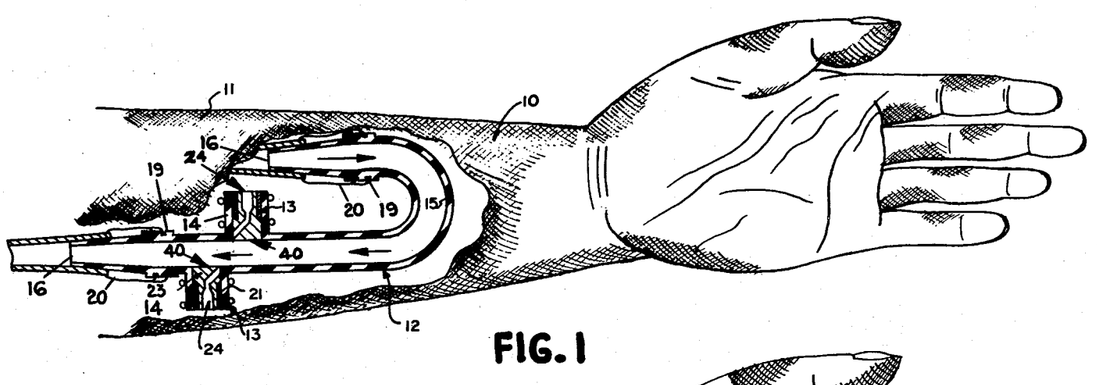
FIG. 1 is a perspective view, partially in section, of a wrist of a human patient showing one embodiment of the shunt of the present invention, disposed beneath the skin with the valves closed.

Referring to FIG. 1, a limb such as a wrist 10 of a patient may be provided with one embodiment of my subcutaneous arterio-venous shunt 12 having valves 13. Shunt 12 comprises a curved tubular member 15 formed of silicone rubber (Silastic) material which terminates at tapered tips or ends 16. Tips 16 are fitted into a vein 17 and an artery 18. Tubular member 15 is J-shaped so that it can be mounted in the arm of a patient with the axis of the tubular member lying in a single plane. This avoids blood turbulence as blood flows through the shunt. In the vicinity of the tips 16, exterior circumferential grooves 19 are provided so that the tips may be anchored to blood vessels 17 and 18 by means of silk ties 20 in a conventional manner.

Shunt 12 is provided with two outlet openings 40, and lateral tubes 14 extend outwardly therefrom. The outlet openings provide fluid communication between the interior and the exterior of the shunt.

Figure 2:
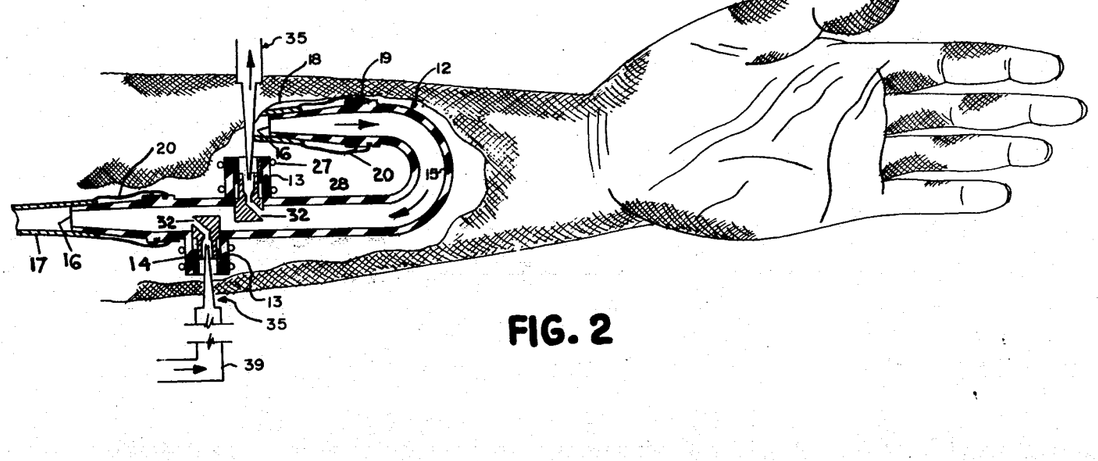
FIG. 2 shows the shunt of FIG. 1 with the valves open.

A valve 13 is secured in each lateral tube. Each valve 13 includes fixed cylindrical housing 21 with an inner double thread 22 and a nested valve member 23 in the form of an internally rotatable cylinder having an exterior circumferential double thread 25 mating with internal double thread 22 on the housing. On rotation, valve member 23 travels axially through housing 21 and extends into the interior of tubular member 15. When extended, an opening 24 through the valve member is exposed to the bloodstream in the shunt and provides fluid communication between the interior and the exterior of the shunt. The fixed cylindrical housings 21 of valves 13 are secured in lateral tubes 14 by the use of retaining rings 27 and 28 or other such means, such as glue.

Figures 3, 6, 7:
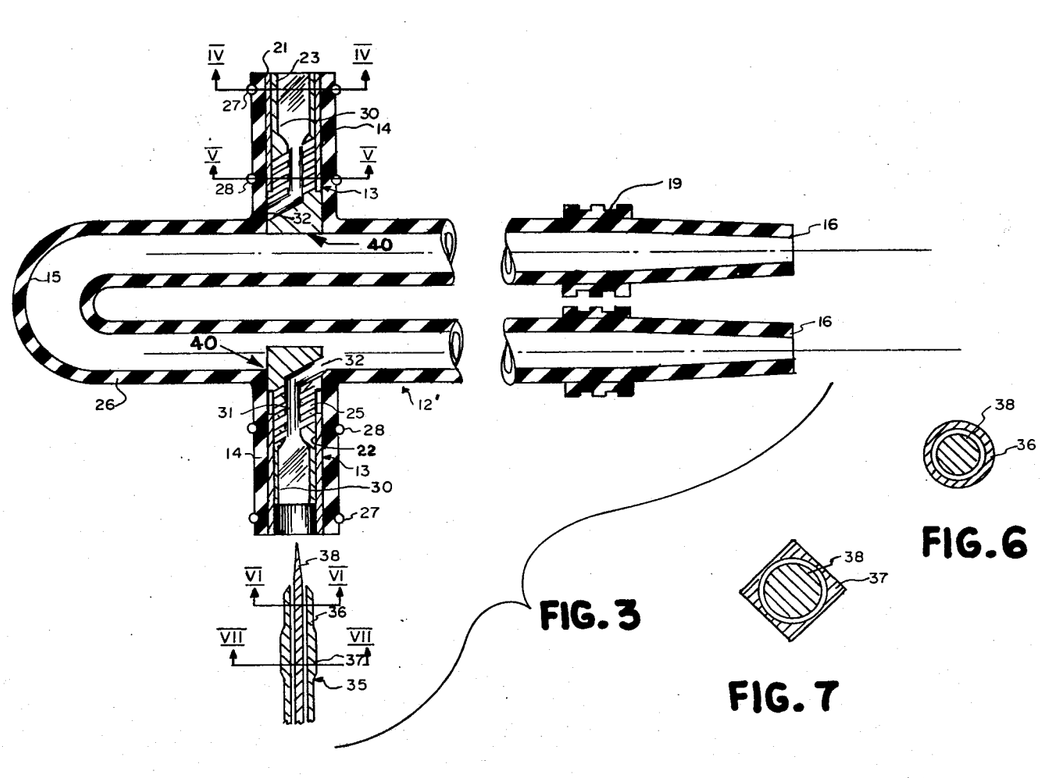
FIG. 3 is an enlarged cross-sectional view showing another embodiment of the valved shunt of the present invention and the needle employed in connection with the valves.
FIGS. 6 and 7, respectively, are sectional views taken along lines VI—VI and VII—VII of FIG. 3.

Referring to FIG. 3, a second embodiment 12' of the shunt of the present invention is shown. This shunt is the same as the J-shaped shunt 12 of FIGS. 1 and 2, except that this shunt comprises a U-shaped tubular member 26 instead of a J-shaped member. This type of shunt is especially suitable for dialyzing humans in the groin region, and as well for animals. Aside from the use of a U-shaped tubular member, shunt 12' is in all other respects the same as shunt 12. For convenience, identical elements are identified with the same numerals used to describe the first embodiment.

As in the first embodiment, shunt 12' includes valves 13 which are embedded in lateral tubes 14 formed of the same Silastic material as tubular member 26. The valves are constrained in lateral tubes 14 by encircling retaining rings 27 and 28.

Figure 4:
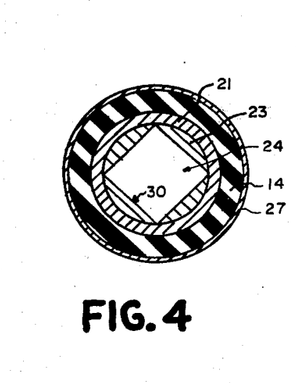
FIGS. 4 and 5, respectively, are sectional views taken along lines IV—IV and V—V of FIG. 3.
Figure 5:
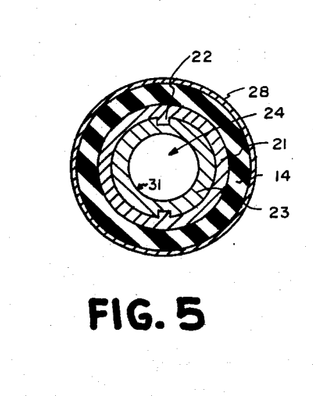
Figure 8:
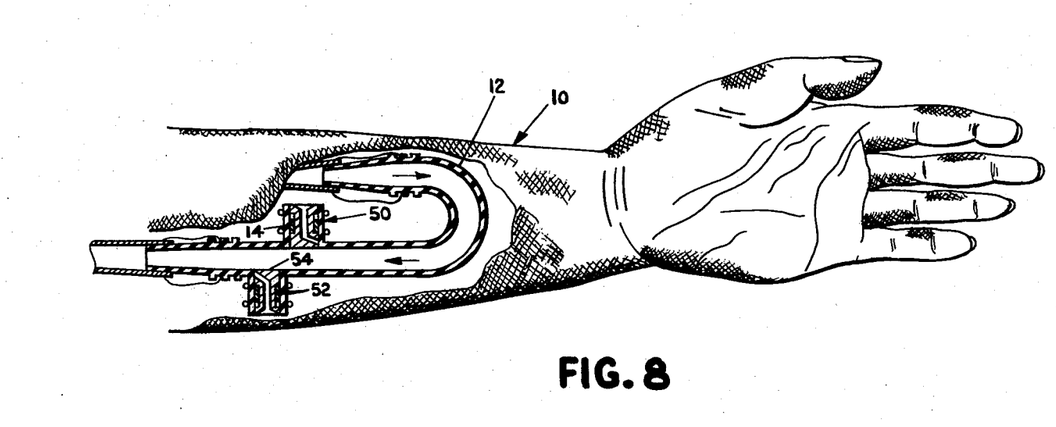
FIG. 8 is a view similar to FIG. 1 of another embodiment of the shunt of the present invention, employing a sliding instead of a rotating valve member.

Rotatable cylinder 23 includes opening 24 therethrough. Opening 24 comprises an external outlet opening 30 at the outer end of the valve member and this opening has a socket region with a non-circular, preferably square, cross-section as shown in FIG. 4. This provides the means for rotating the cylinder 23 as will be explained. The internal end of square socket region is cone shaped and extends into an axial cylindrical portion 31 of circular cross-section as at Section V—V (FIG. 5). The axial portion of the opening then joins an inclined portion that terminates at an internal opening 32 at the side of the valve member adjacent the inner end thereof. When disposed in the interior of tubular member 15 for communication therewith, the valve member is positioned so that internl opening 32 faces upstream or downstream in the bloodstream, depending on whether fluid is to be extracted from or introduced into the bloodstream.

In order to rotate cylinder 23 and to provide circuit connection between the valves 13 and a dialyzer (not shown), the present invention employs a hollow needle 35 having an outer end communicating with the dialyzer and an inner end having a circular tip 36 and a square external profile 37 adjacent but disposed away from the tip. The dimensions of the tip 36 and profile 37 are such that the needle nestingly engages the interior channel 24 of the rotating cylinder 23. Particularly, the profile 37 of the needle mates with the square outlet opening 30 of the valve member and the circular tip 36 of the needle with the circular portion 31. Tip 36 is tapered so as to engage the cone shaped surface at the interface of outlet opening 30 and circular portion 31. The rotation of the needle thus causes the rotation of the cylinder 23. The tight nesting of the circular tip 36 in the outlet opening provides a sealed conduit for the passage of blood from the interior of the shunt through needle 35 without spillage.

In use, a surgical procedure is performed such that the subcutaneous arterio-venous valved shunt of the present invention is implanted in a patient in an appropriate location (e.g., in a patient's wrist or ankle region as in FIGS. 1 and 2), and a vein 17 and artery 18 are secured over the tips 16 by conventional silk ties 20 secured to the severed blood vessels and grooves 19. After implanting the subcutaneous shunt 12, the skin of the patient is sutured closed. The shunt is then available for immediate use in dialysis, although it is preferred that healing take place for a period of about one week.

In implementing a dialysis procedure the following preferably occurs. The skin 11 of the patient at least one inch away from the valves 13 is cleaned in the usual sterile fashion. The valve 13 is felt and gripped between the index finger and thumb to define and locate the valve 13. The skin site for introduction of the needle 35 is marked and a few drops of local anaesthetic injected intradermally. Optionally, a very small longitudinal cut of about 2 millimeters can be made with a sharp scalpel at the site of the introduction of needle 35. This procedure enhances healing of the skin better than lacerations caused by a larger needle penetration.

The needle 35 preferably has disposed within it a stylet 38 to assist in penetration of the needle through the skin and the subcutaneous tissue and to act as well as an index guide for the registering of the needle 35 into the opening 24. On the nesting of the needle 35 in the opening 24, stylet 38 is removed from the needle 35 and the free end of the needle 35 is connected to a primed flexible tubing communicating with the dialyzer. The identical operation is performed in connecting both valves 13 to the dialyzer. The cylinders are respectively rotated 180° to bring the blood of the patient into communication with the dialyzer. The blood will flow from artery 18 through the upstream or arterial valve to the dialyzer and then back through the venous line into the patient through the downstream or venous valve to the vein 17.

On completion of dialysis, the procedure is reversed, that is, the valves 13 are first closed by counter-rotating the cylinders 23 and then the arterial and venous needles are removed.

In the embodiment of the shunt for human wrist application, the tubular member and lateral tubes are molded as a unit of flexible silicone rubber (Silastic), the tubular member thereof being about 3/16 inch to ⅛ inch in internal diameter. Each valve 13 is formed of stainless steel or any other suitable material, and fixed into a lateral tube 14. In place of retaining rings, it is possible to fuse the fixed cylinders of the valves in place by the use of an adhesive or the like. It is preferred that the rotatable cylindrical valve member undergo a rotation of about 180° between open and closed positions, with the axial movement of travel for the rotatable cylinder from open to closed position being approximately ⅛ inch. The needle 35 has an internal diameter of approximately 2 millimeters while the outside diameter of the needle at the square profile is about 3 millimeters.

The valve member is formed in the manner described above for two important reasons. First, it is desirable to have the opening in the side of the valve member fully exposed and facing either directly upstream for withdrawing blood from the system or directly downstream for introducing blood or medication into the system. Thus, a fixed thrust is necessary to insure proper positioning of the opening every time the valve is opened.

Another important reason for the fixed thrust and the shape of the valve member is that it is desirable that when the valve member is fully extended into the interior of the shunt, the valve member not completely cut off the flow of blood through the shunt. If this were the case, a stagnant pocket of blood could form between the arterial and venous outlets, and this stagnation would induce blood clotting. In the present invention, a certain amount of blood continues to flow smoothly around the extended valve member, thus minimizing the risk of clotting in the shunt.

Another feature of the present invention is that it may be cleaned and declotted easily (if clotting should ever occur) by the patient himself by means of a conventional Fogarty catheter. The cleaning and declotting operation is performed simply by fitting the catheter through the hollow needle and the valve when the needle is nested in the valve. In this manner the catheter may be extended into the interior of the shunt and all the way into the blood vessel itself. After it has been fully inserted into the shunt, the Fogarty catheter (which includes an inflatable balloon on the end) may then be inflated to the full diameter of the opening and the catheter withdrawn from the shunt in order to break up and remove any blood that has clotted in the shunt. This is a simple and effective procedure and avoids the complications caused by blood clotting in the prior art shunts.

A second embodiment of the valve mechanism of the present invention is shown in FIGS. 8–11 mounted in the same Silastic tubing employed for valve 13 described above.

Figures 10, 11:
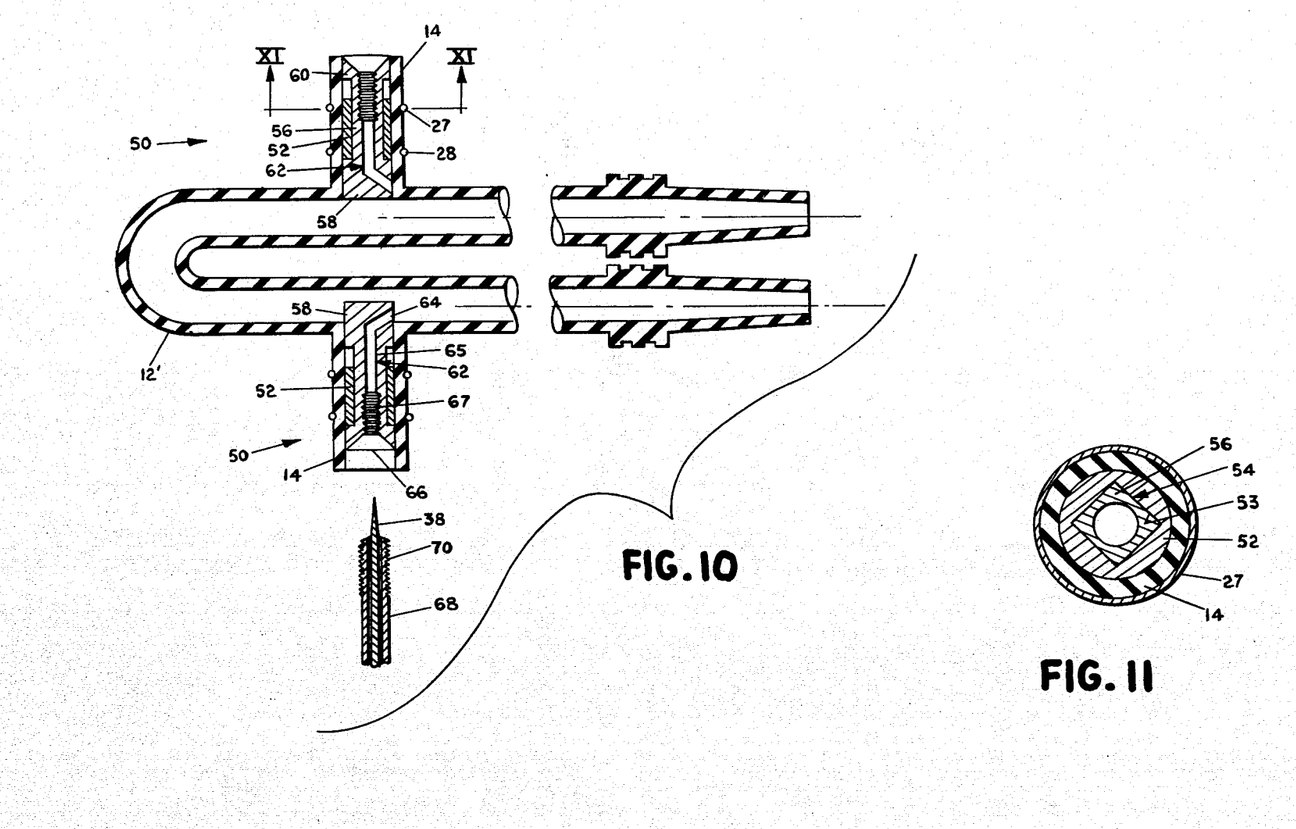
FIG. 10 is an enlarged, broken cross-sectional view of the shunt shown in FIG. 8.
FIG. 11 is a view taken along line XI—XI of FIG. 10

In this embodiment, valve 50 comprises a cylindrical housing 52 having a non-circular (preferably square) axial opening 53 therethrough and a valve member 54 slidably mounted in the axial opening. The housing is centered in lateral tube 14 so as to leave a portion of the tube exposed both above and below the housing. The housing is held in place by retaining rings 27 and 28 or by other means as described above.

The principal difference in the second type of valve is that the valve member is moved inwardly and outwardly by sliding the valve member axially in the housing instead of rotating the valve member in a threaded housing. To accomplish this function, valve member 54 is formed with a non-circular middle section 56 that fits in the non-circular opening in housing 52. Preferably the shape of the middle section is the same as the shape of opening 53, in the housing, so that a smooth non-rotatable fit is achieved. On each side of middle section 56 the valve member is provided with cylindrical collars 58 and 60 at the inner end and outer end of the valve member, respectively. The outer surfaces of the collars are shaped so as to fit snugly in the lateral tube. Since the tube is cylindrical in the described embodiment, the collars similarly are cylindrical. The diameters of the collars are sufficiently large to permit axial movement of the valve member when desired by applying an axial force to the valve member. However, the fit is sufficiently snug to hold the valve member in its desired position and prevent inadvertant opening and closing of the valve. Typically the outer diameters of the collars are the same as the outer diameter of the housing, with this diameter being slightly greater than the inside diameter of the lateral tube.

The respective lengths of middle section 56 and housing 52 are such that the axial movement of the valve member is limited to a distance that just permits full opening and closing of the valve. Engagement of the housing with collars 58 and 60 limits axial movement of the valve member to the stroke desired. Preferably the inner end of the valve is flush with the interior wall of the shunt when the valve is closed, and the valve member protrudes about ⅛ inch into the interior of the shunt when the valve is open.

The valve member is provided with an interior opening 62 substantially the same as the opening in valve member 23 described above. Opening 62 has an inlet opening 64 in the side of the valve member adjacent the inner end. Inlet 64 leads through a tubular conduit 65 to outlet opening 66 at the other end of valve member. The inlet opening preferably is somewhat less than ⅛ inch long and is formed close enough to the end of the valve member, such that the inward movement of the valve member is just enough to fully expose the opening. The snug engagement between the valve member and the lateral tube effectively closes the opening when the valve member is closed.

The principal difference in the opening of valve member 54 and the opening of valve member 23 is the shape of outlet opening 66. Whereas, the outlet opening in valve member 23 is a socket having a non-circlar configuration, outlet opening 66 is conical in shape and has an internally threaded section 67 at the apex of the cone leading into the conduit 65.

The needle employed with the second valve mechanism is a hollow needle 68 as described above, but the needle is provided with a threaded inner end 70 that engages the internally threaded section of the valve member. The conical entrance helps guide the needle into position.

Figure 9:
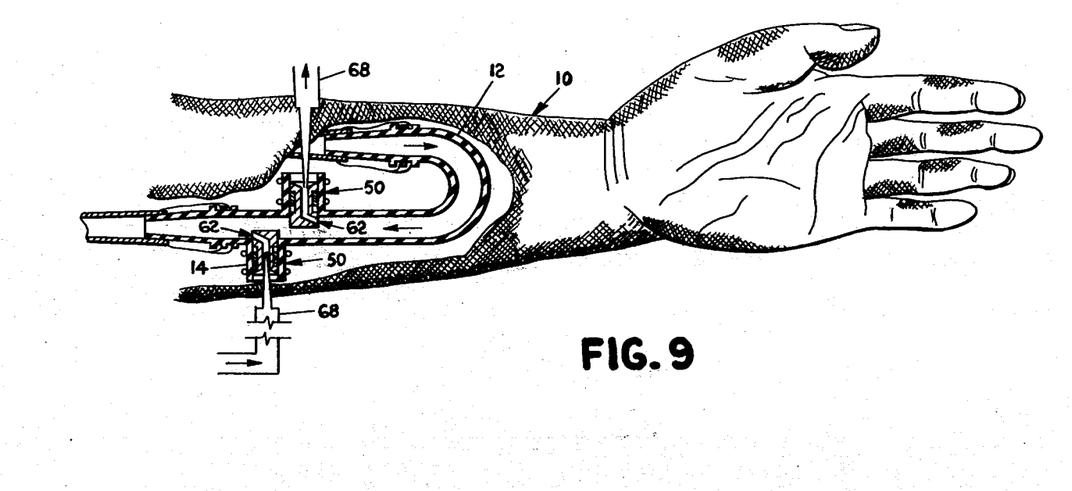
FIG. 9 shows the shunt of FIG. 8 with the needles in place and the shunt open.

In the operation of valve mechanism 50, needle 68 is inserted through the skin as described above and is threaded into the threaded section of inlet 66. The valve is then opened and closed for treatment of a patient by sliding the valve member longitudinally along housing 52. The valve member is not rotated, and inlet opening remains permanently faced in an upstream or downstream direction as desired. After treatment is completed, the valve is closed by pulling on the needle, and then the needle is unscrewed and removed.

It should be understood that the foregoing embodiments are merely exemplary of the preferred practice of the present invention and that various changes and modifications may be made in the arrangements and details of construction of the embodiments described without departing from the spirit and scope of the present invention.

The embodiments of the invention in which an exclusive property or privilege is claimed are defined as follows:

1. Subcutaneous arterio-venous valved shunt means for providing blood access in a patient through a hollow needle intermittently inserted through the skin of the patient, said valved shunt means comprising:
   shunt means for shunting blood from an artery to a vein, said shunt means comprising a subcutaneous tubular member having one end adapted to be connected to an artery and another end adapted to be connected to a vein;
   subcutaneous outlet means in the tubular member adapted to provide fluid communication between the interior and exterior of the shunt means;
   subcutaneous mechanical valve means mounted in the outlet means and having a movable valve member that is movable between an open position, wherein the outlet means is open, and a closed position, wherein the outlet means is blocked, said valve means being adapted to engage and receive the inner end of the hollow needle when it is inserted through the skin, the engagement between the needle and the valve means providing a closed fluid-conducting conduit leading from the interior of the shunt means to the outer end of the hollow needle when the valve means is opened; and
   actuation means for opening and closing the mechanical valve means with the shunt means and valve means mounted entirely subcutaneously in the patient and with the inner end of the needle inserted through the skin and in engagement with the valve means, without providing an additional opening through the skin.

2. Valved shunt means as claimed in claim 1 wherein:

the valve means comprises a tubular housing mounted in the outlet means, said housing having an internal opening therein leading from the interior to the exterior of the shunt means; and the valve member is mounted in the opening in the housing for movement in the housing from its open position, wherein there is fluid communication between the interior and the exterior of the shunt means through the opening in the housing, to its closed position, wherein the opening in the housing is blocked; and the actuation means comprises a releasable interconnection between the hollow needle and the valve member such that the valve member can be opened and closed by manipulation of the hollow needle while it is inserted through the skin of the patient and in engagement with the valve means.

3. Valved shunt means as claimed in claim 1 wherein:

the tubular member of the shunt means is formed of silicone rubber;

the outlet means comprises a cylindrical lateral tube formed of silicone rubber that extends outwardly from an opening in the side of the tubular member;

the valve means comprises a cylindrical housing fitting snugly in the lateral tube and having an axial opening therethrough, with the valve member being movably mounted inside the housing for movement in an axial direction along the opening in the housing between its open and closed positions, the valve member having a fluid-conveying opening therethrough that extends from an outlet in an outer end thereof to an inlet in the side of the valve member at an inner end thereof, the valve member being movable such that the valve member protrudes into the interior of the tubular member when in its open position and is retracted into the outer means when the valve member is in its closed position, the inlet in the valve member being positioned such that the inlet lies at least partially in the interior of the tubular member and is in fluid communcation therewith when the valve member is in its open position, the inlet being retracted in the housing such that it is not in fluid communication with the interior of the tubular member when the valve member is in its closed position, the position of the valve means and valve member further being such that the inlet faces in an upstream direction with respect to the bloodstream when the valve means is employed for removing blood from the patient and faces in a downstream direction with respect to the bloodstream when the valve means is employed for introducing fluids into the patient;

the inner end of the needle is received in the outlet of the opening in the valve member for fluid-conducting engagement with the valve means; and the actuation means comprises a releasable interconnection between the hollow needle and the outlet of the valve member such that the valve member can be opened and closed to selectively provide fluid communication between the interior of the hollow needle and the interior of the shunt means through the opening in the valve member by manual manipulation of the hollow needle while the needle is inserted through the patient's skin and in fluid-conducting engagement with the valve means.

4. Valved shunt means as claimed in claim 1 wherein the shunt means is J-shaped and lies in a single plane, whereby it may be mounted flat in a patient's arm and thereby minimize blood turbulence within the shunt means.

5. Valved shunt means as claimed in claim 1 wherein the shunt means is U-shaped and lies in a single plane so that it may be mounted in the groin of a patient with a minimum of turbulence through the shunt means.

6. Valved shunt means as claimed in claim 1 wherein the shunt means comprises two outlet means spaced axially apart along the tubular member, with separate valve means being mounted in each outlet means, the upstream outlet means being an arterial outlet means for withdrawing blood from the patient and the downstream outlet being a venous outlet means for re-introducing blood back into the patient after treatment.

7. Subcataneous arterio-venous valved shunt means for providing blood access in a patient through a hollow needle intermittently inserted through the skin of te patient, said valved shunt means comprising:

shunt means for shunting blood from an artery to a vein, said shunt means comprising a subcutaneous tubular member having one end adapted to be connected to an artery and another end adapted to be connected to a vein;

subcutaneous outlet means in the tubular member adapted to provide fluid communication between the interior and exterior of the shunt means; and subcutaneous mechaical valve means mounted in the outlet means for selectively opening and closing the outlet means, said valve means including:

a housing mounted in the outlet means and extending outwardly from the shunt means, said housing having an internal culindrial opening therethrough leading from the interior to the exterior of the shunt means; and a valve member movably mounted in the internal opening in the housing for movement in the housing from an open position, wherein there is fluid communication between the interior and exterior of te shunt means through the opening in the housing, to a closed position, wherein the opening in the housing is blocked, the valve member being cylindrical and being axially movable in the housing between its open and closed positions, the outside surface of the valve member and the inside surface of the internal opening in the housing comprising mating thread means adapted to cause longitudinal movement of the valve member with respect to the housing when the valve member is rotated with respect to the housing.

8. Valved shunt means as claimed in claim 7 wherein:

the valve member includes an internal opening therethrough that extends from an outlet in an outer end of the valve member to an inlet in the side of the valve member adjacent an inner end of the valve member; and the valve member is movable from an open position, wherein the inner end extends into the interior of the shunt means and the inlet is exposed to the interior of the shunt means, to a closed position, wherein the inner end of the valve member is retracted into the outlet means and blocked.

9. Valved shunt means as claimed in claim 7 wherein:

the outlet of the opening in the valve member comprises a non-circular profile; and the hollow needle includes a portion adjacent the inner end having a non-circular exterior profile such that the needle fits non-rotatably in said outlet.

10. Valved shunt means as claimed in claim 9 wherein the thread means are double threads and permit full opening and closing of the valve means with the rotation of the valve member through an angle of about 180°.

11. Valved shunt means as claimed in claim 9 wherein the inlet to the opening in the valve member faces the same direction in the shunt every time it is fully opened.

12. Valved shunt means as claimed in claim 11 wherein the valve means is mounted in the outlet means such that the inlet to the opening in the valve member faces upstream in the bloodstream when the valve means is employed for removing blood from the patient, and the valve means is positioned such that the inlet to the opening in the valve member faces downstream in the bloodstream when the valve means is employed for introducing fluids into the bloodstream.

13. Valved shunt means as claimed in claim 11 wherein the valve member permits some blood flow past the valve member when the valve member is open, so as to avoid blood stagnation and possible resultant clotting downstream of the valve means.

14. Subcutaneous arterio-venous valved shunt means for providing blood access in a patient through a hollow needle intermittently inserted through the skin of the patient, said valved shunt means comprising:
  shunt means for shunting blood from an artery to a vein, said shunt means comprising a subcutaneous tubular member having one end adapted to be connected to an artery and another end adapted to be connected to a vein;
  subcutaneous outlet means in the tubular member for providing fluid communication between the interior and exterior of the shunt means; and
  subcutaneous mechanical valve means mounted in the outlet means, said valve means comprising:
    a tubular housing mounted in the outlet means and extending outwardly therefrom, said housing having an internal opening therethrough leading from the interior to the exterior of the shunt means;
    a valve member axially movable in the internal opening of the housing for movement from a closed position, wherein the valve member is withdrawn from the interior of the shunt means, to an open position, wherein the valve member protrudes into the interior of the shunt means, the valve member having an opening therethrough that provides fluid communication between the interior and exterior of the shunt means, said opening means having an inlet at an inner end of the valve member adjacent the interior of the shunt means and an outlet in an outer end of the valve member at the exterior of the shunt means, the inlet being formed inside of the valve member such that the inlet is exposed to and in fluid communication with the interior of the shunt means only when the valve member is in its open position and protrudes into the interior of the shunt means, the inlet being withdrawn and not exposed to the interior of the shunt means when the valve member is in its closed position.

15. Valved shunt means according to claim 14 wherein the axial movement of travel of the valve member is such that the distance that the valve member protrudes into the interior of the shunt means when in its open position is limited so as to permit flow of blood through the shunt means while the valve member is in its open position.

16. Valved shunt means as claimed in claim 14 wherein:
  the valve member is axially slidable and not rotatable in the housing between its open and closed positions; and
  the outlet of the opening in the valve member has a threaded interor portion; and
  the end of the needle is threaded so as to be engagable with the threaded portion of said outlet, the actuation means for opening or closing the valve being an axial force applied on the valve member by applying said force in an inwardly or outward direction on the needle.

17. Valved shunt means as claimed in claim 16 wherein the valve member includes collar means for engaging the housing and limiting the inward and outward movement of the valve member to the distance necessary to open and close the valve means.

18. Valved shunt means as claimed in claim 17 wherein the outlet of the valve member includes an outwardly extending cone means, and the threaded portion is positioned at the apex of the cone means, the cone means receiving and guiding the end of the needle into threaded engagement with the threaded portion of the outlet.

19. Valved shunt means as claimed in claim 16 wherein:
  the shunt means is formed of tubular silicone rubber and the outlet means comprises a hollow outlet tube of silicone rubber extending outwardly from the shunt means;
  the housing is formed such that it fits snugly in a fixed position in the outlet tube;
  the valve member includes a middle portion, that slidably fits through the opening in the housing, and collars at each end of the middle portion, said collars extending outwardly into resilient engagement with the outlet tube, the engagement between the valve member and the outlet tube providing frictional resistance sufficient to prevent the valve means from opening or closing except when desired by applying pressure on a needle lodged in the inlet of the valve member opening, said collars also serving to engage the ends of the housing so as to limit the axial stroke of the valve member to the distance required to fully open and fully close the valve member.

20. Valved shunt means as claimed in claim 14 wherein the valve means is mounted in the outlet means such that the inlet to the opening in the valve member faces upstream in the bloodstream when the valve means is employed for removing blood from the patient, and the valve means is positioned such that the inlet to the opening in the valve member faces downstream in the bloodstream when the valve means is employed for inroducing fluids into the bloodstream.

21. Valved shunt means as claimed in claim 14 wherein the valve member permits some blood flow past the valve member when the valve member is open, so as to avoid blood stagnation and possible resultant clotting downstream of the valve means.

22. A method for providing blood access in a patient through a hollow needle intermittently inserted through the skin of the patient comprising the following steps:
- connecting a subcutaneous arterio-venous shunt between an artery and a vein in the patient;
- providing a subcutaneous outlet in the shunt that provides fluid communication between the interior and the exterior of the shunt;
- mounting a mechanical valve subcutaneously in the outlet of the shunt, the mechanical valve being of the type that has a movable valve member that is movable between an open position, wherein the outlet is open, and a closed position, wherein the outlet is blocked, the valve being formed so as to engage and receive the inner end of the hollow needle in fluid-conducting engagement therewith when the needle is inserted through the skin, the engagement between the needle and valve means providing a closed fluid-conducting conduit leading from the interior of the shunt means to the outer end of the hollow needle when the valve means is open, the valve being such that it is actuable for movement between its open and closed position by manipulation of the needle when the needle is in fluid-conducting engagement with the valve; and
- inserting the hollow needle through the skin of the patient into fluid conducting engagement with the valve, the needle being formed such that when the needle is in fluid-conducting engagement with the valve, there is a mechanical interconnection between the needle and the valve that makes it possible to open and close the valve by manipulation of the needle.

* * * * *